United States Patent [19]
Johnson

[11] 4,051,147
[45] Sept. 27, 1977

[54] 1-(ARYLAMINO)-AND 1-(ARYLIMINO)-PYRROLES

[75] Inventor: Robert E. Johnson, East Greenbush, N.Y.

[73] Assignee: Sterling Drug Inc., New York, N.Y.

[21] Appl. No.: 585,448

[22] Filed: June 9, 1975

Related U.S. Application Data

[63] Continuation-in-part of Ser. No. 372,324, June 21, 1973, abandoned.

[30] Foreign Application Priority Data

June 10, 1974 United Kingdom ............... 25599/74

[51] Int. Cl.² .......................................... C07D 207/50
[52] U.S. Cl. ......................... 260/326.47; 260/326.25; 260/326.33; 260/326.5 R; 260/326.5 J; 260/326.5 C; 260/326.5 L; 260/326.9; 260/566 R; 260/569; 260/574; 421/274; 548/359
[58] Field of Search ..................... 260/326.33, 326.47, 260/326.5 C, 326.5 L

[56] References Cited

U.S. PATENT DOCUMENTS 2,725,378  11/1955  Reed ................................. 260/313.1

OTHER PUBLICATIONS

Grammaticakis; Chem. Abstr., vol. 75; 35577u, (1971).

Primary Examiner—Donald G. Daus
Assistant Examiner—Mary C. Vaughn
Attorney, Agent, or Firm—William G. Webb; B. Woodrow Wyatt

[57] ABSTRACT 1-(Arylamino)pyrroles and 1-(arylimino)pyrroles, useful as antibacterial agents, are prepared by reaction of an arylhydrazine or arylhydrazone with a 2,5-di-loweralkoxytetrahydrofuran or with an alkanedione; by reaction of a 1-arylaminopyrrole with an oxalyl dihalide followed by oxidative hydrolysis of the product; by condensation of a 1-aminopyrrole with a quinone; or by oxidation or reduction of a respective 1-(arylamino)pyrrole or 1-(arylimino)pyrrole.

12 Claims, No Drawings

1-(ARYLAMINO)-AND 1-(ARYLIMINO)-PYRROLES

Related Applications

This is a continuation-in-part of my prior, copending application, Ser. No. 371,324, filed June 21, 1973, now abandoned.

BACKGROUND OF THE INVENTION a. Field of the Invention

This invention relates to 1-(arylamino) pyrroles and 1-(arylimino)pyrroles useful as antibacterial agents.

b. Description of the Prior Art

The compound, 1-phenylamino-2,5-dimethylpyrrole, is described by Reed U.S. Pat. No. 2,725,378 (patented Nov. 29, 1955 on an application filed Sept. 19, 1951) as an intermediate for the preparation of monomethine cyanine dyes and is not known to have any other utility than as an intermediate. I have found this compound to be inactive as an antibacterial agent.

SUMMARY OF THE INVENTION

In a composition of matter aspect, the invention relates to 1-(arylamino)- and 1-(arylimino) pyrroles useful as antibacterial agents.

In another composition of matter aspect, the invention relates to the species, 1-(phenylamino)pyrrole, useful as a urinary antiseptic agent.

In one of its process aspects, the invention relates to a process for preparing 1-(arylamino)pyrroles unsubstituted in both the 2- and 5-positions which comprises reacting an arylhydrazine with a 2,5-di-lower-alkoxytetrahydrofuran.

In another of its process aspects, the invention relates to a process for preparing 1-(arylamino)pyrroles unsubstituted in both the 2-and 5-positions which comprises reacting a 1-aryl-2-lower-alkanehydrazone with a 2,5-di-lower-alkoxytetrahydrofuran.

In another of its process aspects, the invention relates to a process for preparing 1-(arylamino)pyrroles substituted in both the 2- and 5-positions with a lower-alkyl group which comprises reacting an arylhydrazine with an alkanedione.

In another of its process aspects, the invention relates to a process for preparing 1-(arylamino)pyrroles substituted at the 2-position by a carboxyl group and unsubstituted at the 5-position which comprises reacting a 1-arylaminopyrrole with an oxalyl dihalide and reacting the resulting 2-arylpyrrolo[1,2-b]pyrazole-3,4-dione with hydrogen peroxide in the presence of aqueous alkali.

In another of its process aspects, the invention relates to a process for preparing a 1-(quinon-1-ylimino)pyrrole which comprises reacting, in the presence of a strong acid, a 1-amino-pyrrole with a quinone, for example a benzoquinone or a naphthoquinone.

In another of its process aspects, the invention relates to a process for preparing a 1-(arylimino)pyrrole which comprises oxidizing, with mercuric oxide, silver nitrate or silver oxide, a corresponding 1-arylaminopyrrole.

In another of its process aspects, the invention relates to a process for preparing a 1-(4-nitrosoarylamino)pyrrole which comprises reacting a 1-aminopyrrole with a 4-nitrosoarylphenol derivative in the presence of toluenesulfonic acid.

In another of its process aspects, the invention relates to a process for preparing a 1-(arylamino)pyrrole which comprises reducing a 1-(arylimino)pyrrole with an alkali metal bisulfite.

In another of its process aspects, the invention relates to a process for preparing a 1,1'-(1,4-quinonyldiimino)-dipyrrole which comprises reacting a 1-aminopyrrole with a quinone in the presence of an acid catalyst.

DETAILED DESCRIPTION INCLUSIVE OF THE PREFERRED EMBODIMENTS

More specifically, this invention relates to 1-(arylamino)pyrroles and 1-(arylimino)pyrroles, which are generally useful as antibacterial agents, and which have the respective formulas Ia, Ib, Ic and Id:

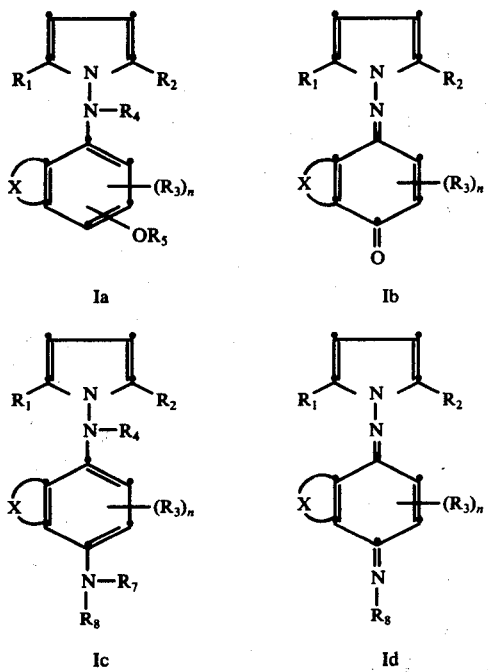

where $R_1$ and $R_2$ are each hydrogen or each lower-alkyl, or $R_1$ is hydrogen and $R_2$ is carboxyl; $R_3$ is hydrogen, hydroxy, benzyloxy, halogen (including fluorine, chlorine and bromine), azido, amino, di-lower-alkylamino or lower-alkyl; $R_4$ is hydrogen, lower-alkanoyl, benzoyl or lower-alkyl; X represents either a benzenoid nucleus fused to the phenyl ring at the positions indicated, or it represents two hydrogen atoms, or one hydrogen atom and one of the groups $R_3$, or two of the groups $R_3$; $R_5$ is hydrogen, lower-alkyl, lower-alkanoyl, benzoyl or benzyl; $R_7$ is hydrogen; $R_8$ is lower-alkyl, phenyl or 1-pyrrolyl, or $R_7$ and $R_8$ taken together with the nitrogen atom to which they are attached represent nitroso (N=O); $n$ is one of the integers 1 and 2, and where the phenyl ring of the groups $R_4$ and $R_5$ when benzoyl or of the $R_8$ group when phenyl can be substituted by lower-alkyl, lower alkoxy or from one to two halogens (including fluorine, chlorine or bromine).

As used herein, the terms lower-alkyl, lower-alkoxy or lower-alkanoyl mean saturated, monovalent, aliphatic radicals, including straight or branched-chain radicals, of from one to four carbon atoms, as illustrated by methyl, ethyl, propyl, isopropyl, butyl, sec. -butyl, isobutyl, t-butyl, methoxy, ethoxy, isopropoxy, butoxy, formyl, acetyl, propionyl, butyryl and isobutyryl.

The compounds of formulas Ia and Ic are prepared by a variety of methods, the choice of which will depend upon the identity of the premutations $R_1$ and $R_2$. These methods are described as follows:

METHOD A

Condensation of an arylhydrazine with a 2,5-di-lower-alkoxytetrahydrofuran

This method, useful for the preparation of compounds of formulas Ia or Ic where $R_1$ and $R_2$ are both hydrogen, comprises reacting an arylhydrazine of formulas IIa or IIc, respectively, with a 2,5-di-lower-alkoxytetrahydrofuran of formula III, and is represented by the following reactions:

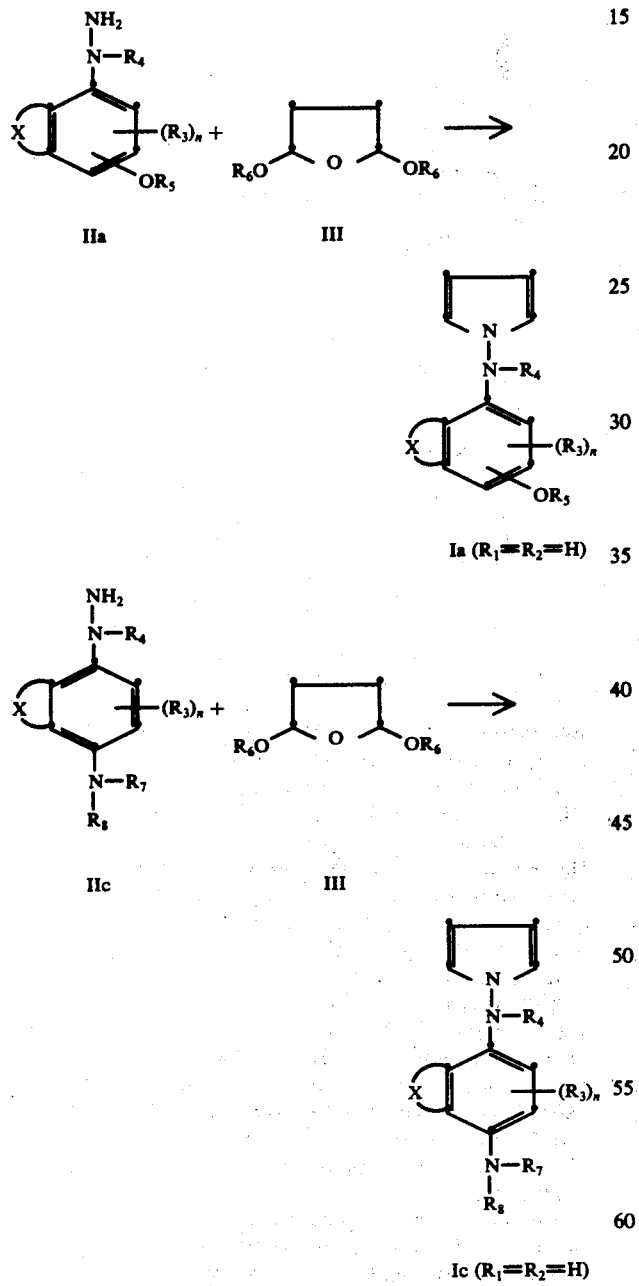

Ic ($R_1 = R_2 = H$)

where $R_3$, $R_4$, $R_5$, $R_7$, $R_8$, X and n have the meanings given above, and $R_6$ is lower-alkyl. The reaction is preferably carried out in an acid medium, for example a lower-alkanoic acid such as acetic acid. Although the reaction takes place at ambient temperature, the reaction rate is increased at elevated temperatures, and therefore it is advantageous to carry out the reaction at temperatures from 50° C. to approximately 100° C.

METHOD B

Condensation of a 1-aryl-2-lower alkanehydrazone with a 2,5-di-lower-alkoxytetrahydrofuran This method, useful for the preparation of compounds of formulas Ia or Ic where $R_1$ and $R_2$ are both hydrogen, comprises reacting a 1-aryl-2-lower-alkanehydrazone of formulas IVa or IVc, respectively, with a 2,5-di-lower-alkoxytetrahydrofuran of formula III, and is represented by the reactions:

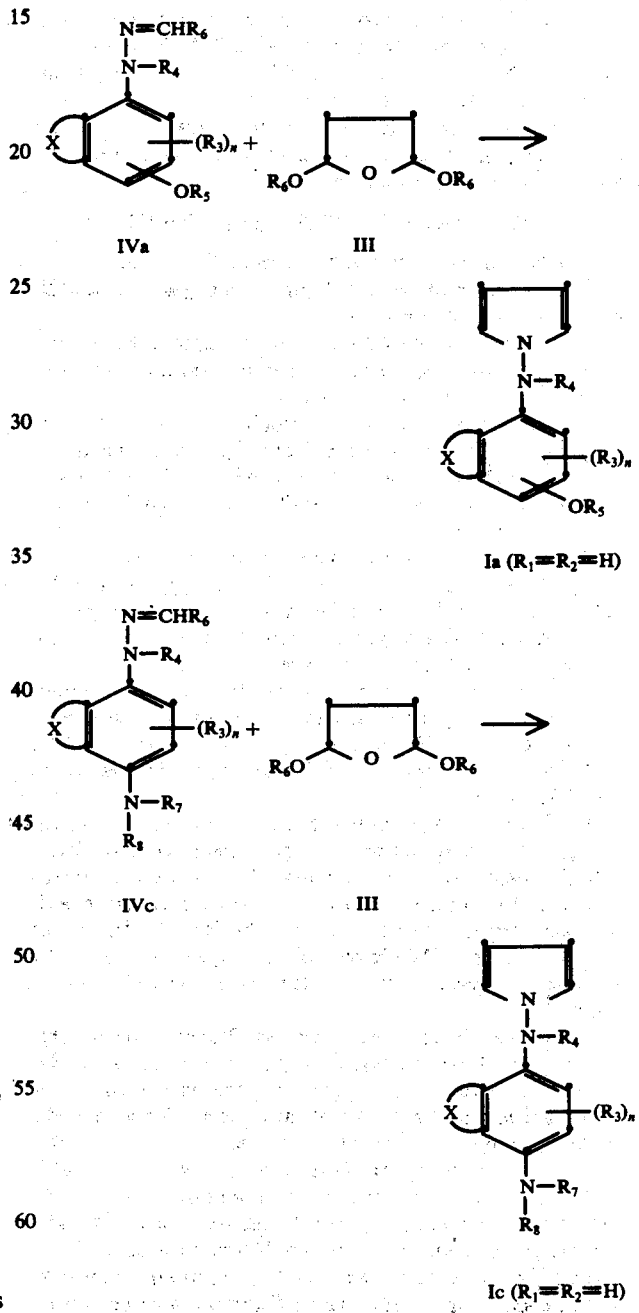

Ic ($R_1 = R_2 = H$)

where $R_3$, $R_4$, $R_5$, $R_6$, $R_7$, $R_8$, X and n have the meanings given above. The reaction is carried out under essentially the same conditions described above for Method A.

METHOD C

Condensation of an arylhydrazine with an alkanedione

This method, which is useful for the preparation of compounds of formulas Ia or Ic where $R_1$ and $R_2$ are both lower-alkyl, comprises reacting an arylhydrazine of formulas IIa or IIc, respectively, with an alkanedione of formula V, and is represented by the following reactions:

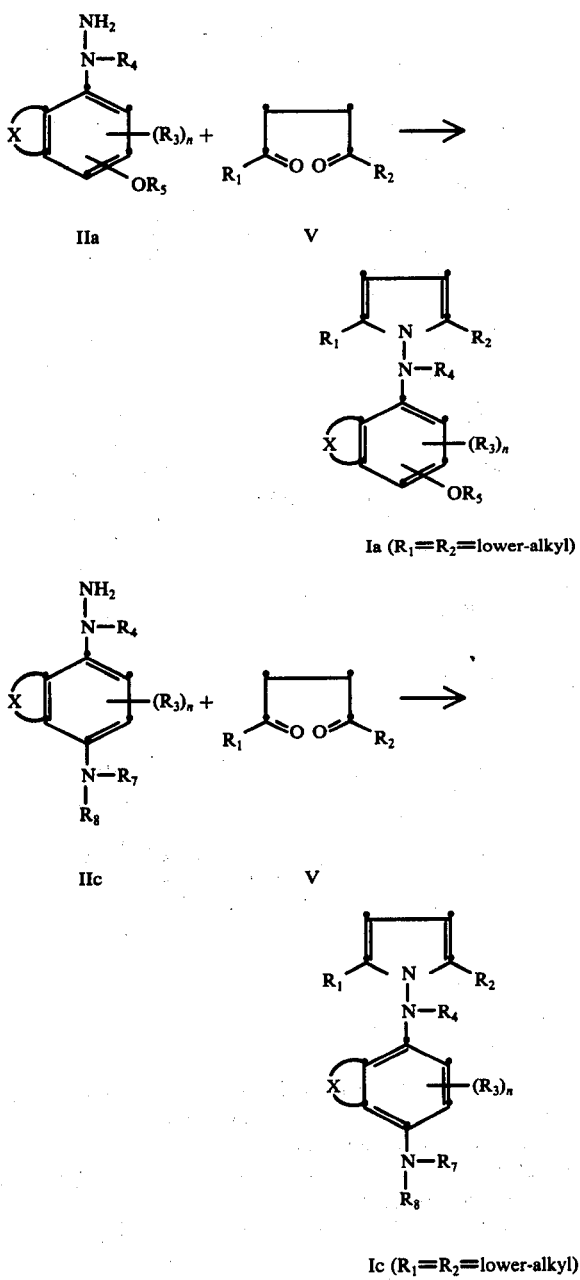

Ia ($R_1 = R_2 =$ lower-alkyl)

Ic ($R_1 = R_2 =$ lower-alkyl)

where $R_1$, $R_2$, $R_3$, $R_4$, $R_5$, $R_6$, $R_7$, $R_8$, X and n have the meanings given above. The reaction is carried out under the same conditions described above for Method A.

In each of the above Methods A, B and C it is preferred to carry out the cyclization with arylhydrazines (or 1-aryl-2-lower-alkanehydrazones) in which the group $R_4$ is other than hydrogen, i.e. either lower-alkyl, lower-alkanoyl or benzoyl, the lower-alkanoyl or benzoyl compounds being used when it is desired to produce final products of formulas Ia or Ic where $R_4$ is hydrogen, because, as will be described hereinafter, the compounds of formulas Ia or Ic where $R_4$ is hydrogen can be produced from the corresponding compounds where $R_4$ is lower-alkanoyl or benzoyl by alkaline hydrolysis of the lower-alkanoyl or benzoyl group. In Method C described above, the compounds of formulas Ia or Ic where $R_4$ is hydrogen can be produced directly by use of an arylhydrazine of formulas IIa or IIc, respectively, in which $R_4$ is hydrogen, but the yields of final product are generally lower than those obtained in the overall process involving hydrolysis of the lower-alkanoyl or benzoyl group.

METHOD D

Condensation of a 1-arylaminopyrrole with an oxalyl dihalide and oxidative hydrolysis of the resulting 2-arylpyrrolo[1,2-b]pyrazole-3,4-dione This method, which is useful for the preparation of the compounds of formula Ia where $R_1$ is hydrogen and $R_2$ is carboxyl, comprises reacting a 1-arylaminopyrrole of formula Ia where $R_1$, $R_2$ and $R_4$ are each hydrogen with an oxalyl halide and reaction of the resulting 2-arylpyrrolo[1,2-b]pyrazole-3,4-dione of formula VI with hydrogen peroxide in the presence of aqueous alkali. The method is represented by the following reaction sequence:

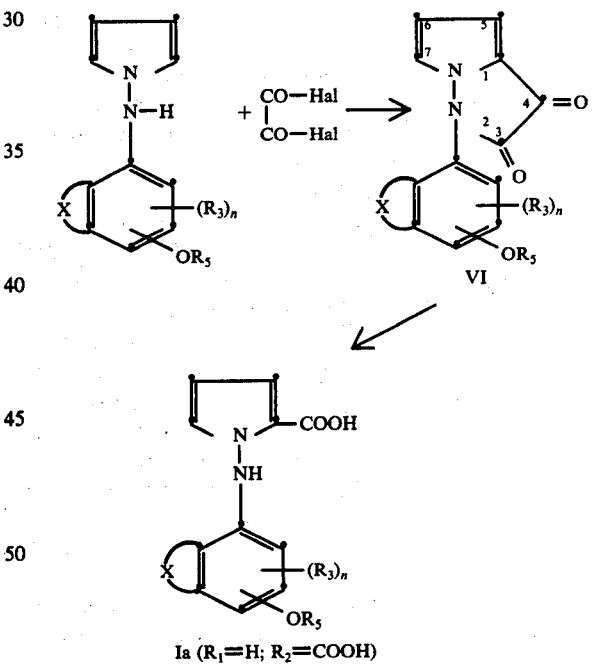

Ia ($R_1 =$ H; $R_2 =$ COOH)

where $R_3$, $R_5$, X and n have the meanings given above, and Hal is halogen. The condensation of the 1-arylaminopyrrole with the oxalyl halide is preferably carried out in an organic solvent inert under the conditions of the reaction, for example diethyl ether, tetrahydrofuran, dioxane, and the like, and at a temperature in the range from $-20°$ C. to $+20°$ C. The oxidative hydrolysis of the 2-arylpyrrolo[1,2-b]pyrazole-3,4-dione is carried out in an aqueous medium at a temperature from $0°$ C. to about $50°$ C.

As indicated above, the compounds of formulas Ia or Ic where $R_4$ is hydrogen are advantageously prepared by hydrolysis of the corresponding compounds where $R_4$ is lower-alkanoyl or benzoyl, and in fact, the latter compounds are primarily useful as intermediates for preparing the therapeutically active compounds. The hydrolysis is generally carried out by warming a solution of the amide in a lower-alkanol containing at least one molar equivalent of an alkali metal hydroxide.

Moreover, the compounds of formula I$a$ where $R_5$ is hydrogen and $R_3$ is hydrogen or hydroxy are advantageously prepared by catalytic hyrogenolysis of the corresponding benzyloxy ethers of the final products ($R_5$ is benzyl and/or $R_3$ is hydrogen or benzyloxy), and thus the benzyloxy ethers are useful as intermediates for the preparation of the final products. The hydrogenolysis is carried out by reduction of the benzyloxy compound dissolved in an inert organic solvent, for example a lower-alkanol such as methanol, ethanol or isopropanol, and in the presence of a catalyst, a preferred catalyst being palladium-on-charcoal. Reduction takes place at temperatures in the range from 20° C. to approximately 100° C. and at pressures from 10 to 50 p.s.i.

The compounds of formula I$a$ where $R_5$ is a lower-alkanoyl or benzoyl group are preferably prepared by reaction of the corresponding compounds where $R_5$ is hydrogen with a suitable alkanoylating or benzoylating agent, respectively, e.g., with either a molor equivalent amount of a benzoyl halide or with a molar excess of a lower-alkanoic acid anhydride in the presence of pyridine. The reaction takes place at ambient temperature in a molar excess of the pyridine as solvent.

The compounds of formulas I$a$ and I$c$ wherein $R_4$ is lower-alkanoyl or benzoyl can be obtained by reacting the corresponding compounds wherein $R_4$ is hydrogen and $R_5$ is other than hydrogen with a suitable alkanoylating or benzoylating agent, respectively. The compounds of formula I$a$ where both $R_4$ and $R_5$ are benzoyl are produced in the reaction when $R_4$ and $R_5$ are both hydrogen in the starting material and when two or more molar equivalents of the benzoyl halide are used in the reaction. The compounds of formulas I$a$ or I$c$ where $R_4$ is lower-alkanoyl can also be prepared from the compounds where $R_4$ is hydrogen and $R_5$ is hydrogen by reaction of the latter with an alkali metal hydride is an inert organic solvent and reaction of the resulting alkali metal salt with a lower-alkanoic acid anhydride. The reaction takes place at temperatures from 0°–25° C. A preferred solvent is dimethylformamide (DMF).

The arylhydrazines of formulas II$a$ and II$c$, which are used as intermediates in Methods A and C, are prepared from the known corresponding arylamines of formulas VII$a$ or VII$c$ by one of several methods, the choice of which depends on the nature and identity of the group $R_4$. One such method, useful for preparing the compounds where $R_4$ is benzoyl comprises reacting an arylhydrazine of formulas II$a$ or II$c$ where $R_4$ is hydrogen with a lower-alkanealdehyde and reaction of the resulting 1-aryl-2-lower-alkanehydrazone of formulas IV$a$ or IV$c$, respectively, above ($R_4$ is hydrogen) with a benzoyl halide in the presence of an organic base such as triethylamine or pyridine, followed by hydrolysis of the resulting hydrazone with dilute acid in a lower-alkanol. The method is represented by the reaction sequences:

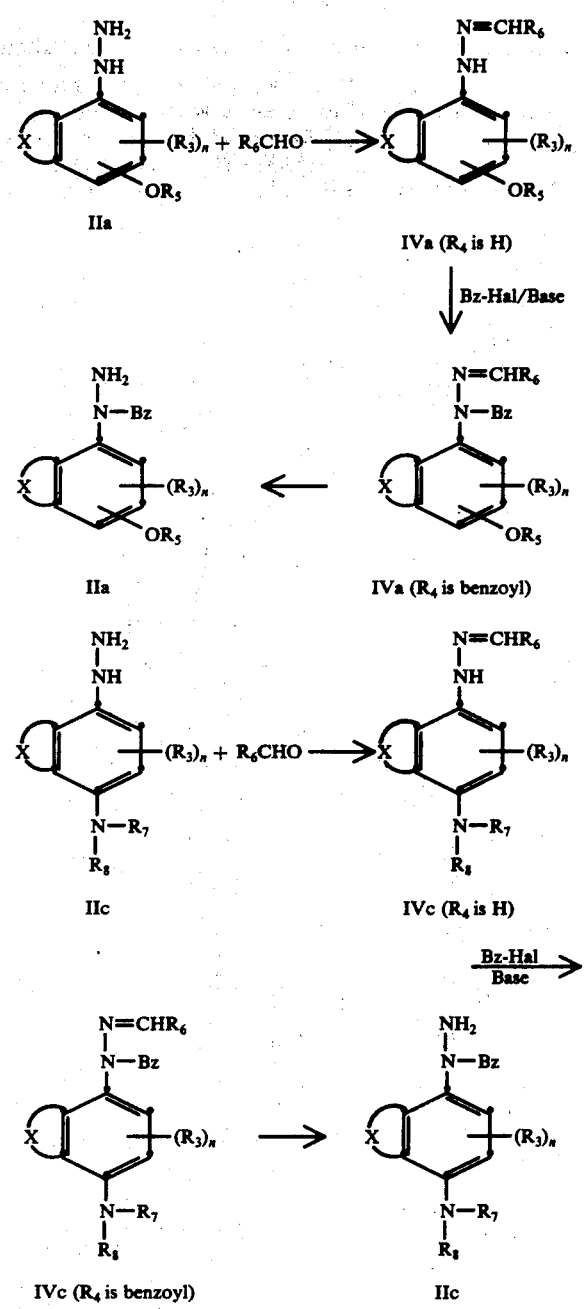

where $R_3$, $R_5$, $R_6$, $R_7$, $R_8$, X and $n$ have the meanings given above, and Bz represents benzoyl. The formation of the hydrazone takes place by simply mixing solutions of the arylhydrazine and the aldehyde in an inert organic solvent, for example a lower-alkanol. The benzoylation is effected by adding a molar equivalent of the benzoyl halide to a solution of the hydrazone in the organic base at a temperature from 0° to 20° C. A preferred base is pyridine. The hydrolysis of the hydrazone takes place at ambient temperature in a solution containing dilute mineral acid.

Another method for preparing the arylhydrazines of formula II$a$, which is useful for preparing the compounds where $R_4$ is lower-alkyl, comprises N-nitrosation with an aqueous alkali metal nitrite in the presence of a mineral acid of an appropriate N-lower-alkylarylamine of formula VII$a$ and reduction, either catalytically or chemically, of the resulting N-nitroso-N-lower-alkylarylamine of formula VIII. The method is represented by the following reaction scheme:

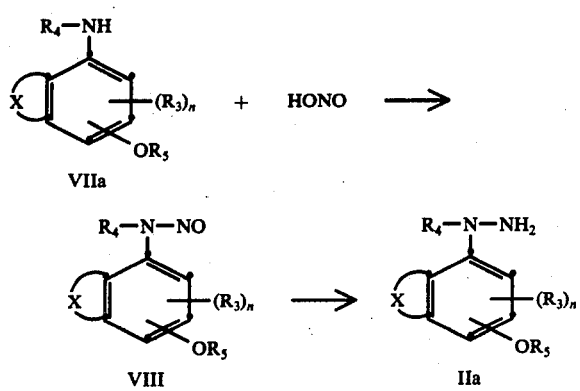

where $R_3$, $R_5$, X and $n$ have the meanings given above, and $R_4$ is lower-alkyl. The nitrosation is carried out by dissolving the amine in cold (0°–10° C.) aqueous dilute mineral acid and adding an aqueous solution of an alkali metal nitrite. Catalytic reduction of the nitroso compound is best effected over palladium-on-charcoal at ambient temperature and at hydrogen pressures in the range from 10 to 50 p.s.i. and in an inert organic solvent, for example a lower-alkanol. Chemical reduction is effected with an alkali metal aluminum hydride in an inert organic solvent, for example diethyl ether, dioxane or tetrahydrofuran.

Finally the compounds of formula IIa where $R_4$ is either lower-alkyl, lower-alkanoyl or benzoyl are prepared by reacting an appropriate N-benzoyl-N-lower-alkanoyl- or N-lower-alkylarylamine with chloramine. In the case of the N-benzoyl or N-lower-alkanoyl compounds, it is necessary to first react the N-lower-alkanoyl- or N-benzoylarylamine with a strong base, for example an alkali metal hydride, to form an alkali metal salt which is then reacted with the chloramine. The method is represented by the following reaction scheme:

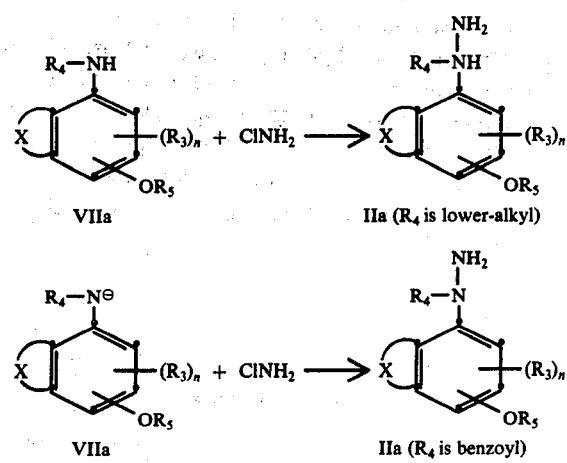

where $R_3$, $R_5$, X and $n$ have the meanings given above, and $R_4$ has the particular meanings designated in the reaction scheme.

The 2,5-di-lower-alkoxytetrahydrofurans of formula III and the alkanediones of formula V are generally known classes of compounds and are prepared by methods well-known in the art.

The final products of formulas Ib and Ib are prepared by one of two possible methods described as follows:

METHOD E

Condensation of a 1-aminopyrrole with a quinone

This method comprises reacting, in the presence of a strong acid, e.g. aqueous mineral acid, or alcoholic trifluoro-acetic acid or toluenesulfonic acid, a 1-aminopyrrole of formula IX with an appropriate quinone of formula X according to the reaction:

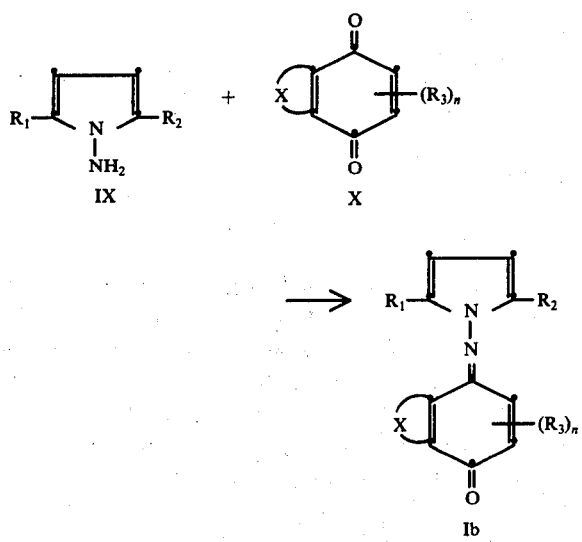

where $R_1$, $R_2$, $R_3$, X and $n$ have the meanings given above. The reaction takes place readily at ambient temperature when an aqueous solution of the aminopyrrole in dilute aqueous acid is mixed with a solution of the quinone in either water or aqueous lower-alkanol. A preferred strong acid is trifluoroacetic acid. The compounds of formula Id where $R_8$ is 1-pyrrolyl are produced in the reaction as a by-product, especially when a molar excess of the starting 1-aminopyrrole is used. The compounds of formula Id, however, are preferably prepared by another method to be described hereinafter.

METHOD F

Oxidation of a 1-arylaminopyrrole

This method for preparing compounds of formulas Ib and Id comprises oxidation of a 1-arylaminopyrrole of formulas Ia or Ic, respectively, in which $R_4$ is hydrogen, $R_5$ is hydrogen, the $R_5O$ group is attached to the 4-position of the aryl ring with respect to the imine bridge, and $R_7$ is hydrogen. The method is represented by the reactions:

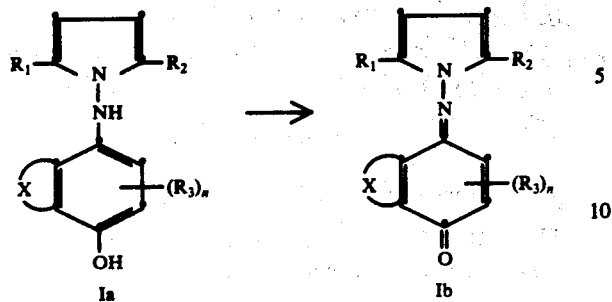

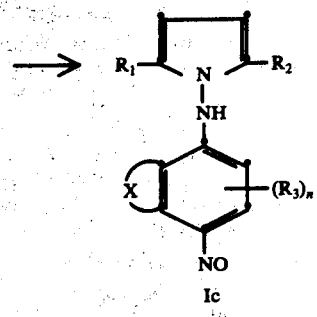

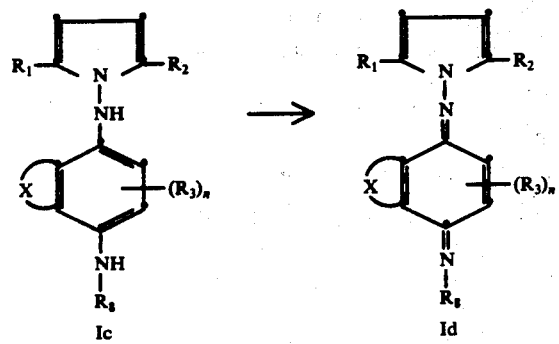

where $R_1$, $R_2$, $R_3$, $R_8$, X and n have the meanings given above. The reaction is carried out using mercuric oxide, silver nitrate or silver oxide as the oxidizing agent and in an organic solvent inert under the conditions of the reaction, for example, benzene, toluene, xylene, a lower-alkanol, for example, ethanol or acetone. The reaction is advantageously carried out at the reflux temperature of the solvent used.

The 1-aminopyrroles of formula IX and the quinones of formula X are generally known classes of compounds which are prepared by methods well-known in the art.

In addition to the methods described above, the compounds of formula Ic are also prepared by one of two other methods depending upon the specific definitions of the groups $R_4$, $R_7$ and $R_8$.

METHOD G

Arylation of a 1-aminopyrrole

The compounds of formula Ic where $R_4$ is hydrogen and $R_7$ and $R_8$ taken together with the nitrogen atom represent nitroso are prepared by reaction of a 1-aminopyrrole of formula IX with a 4-nitrosoarylphenol derivative of the formula XI in the presence of toluenesulfonic acid. The reaction is represented by the reaction:

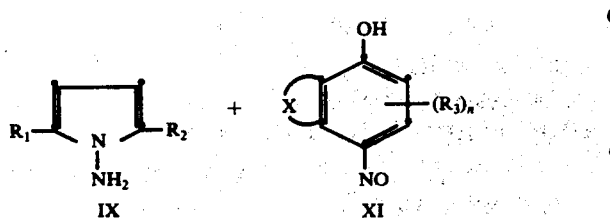

where $R_1$, $R_2$, $R_3$, X and n have the meanings given above. The reaction is preferably carried out in an inert organic solvent such as methanol, ethanol or isopropanol.

METHOD H

Reduction of a 1-(arylimino)pyrrole

The compounds of formula Ic where $R_4$ and $R_7$ are both hydrogen are prepared from the corresponding compounds of formula Id by reduction of the latter in an aqueous lower-alkanol with an alkali metal hydrosulfite.

One method for the preparation of the compounds of formula Id has been described above. A preferred method is as follows:

METHOD J

Reaction of a quinone with a 1-aminopyrrole

As indicated above, the compounds of formula Id where $R_8$ is 1-pyrrolyl are produced as a by-product when a 1-aminopyrrole of formula IX is reacted with a quinone of formula X in aqueous acid or aqueous lower-alkanol in the presence of an acid catalyst. The compounds can be obtained in better yield if the reaction is carried out in diethyl ether in the presence of an acid-catalyst, particularly trifluoroacetic acid.

The compounds of formulas Ia or Ic where $R_3$ is halogen, $R_4$ and $R_5$ are hydrogen, and n is 1 are advantageously prepared by reaction of the corresponding compounds of formulas Ib or Id, respectively, where $R_3$ is hydrogen with an anhydrous hydrohalic acid in an inert organic solvent, for example diethyl ether, tetrahydrofuran or dioxane. The process is represented by the reactions:

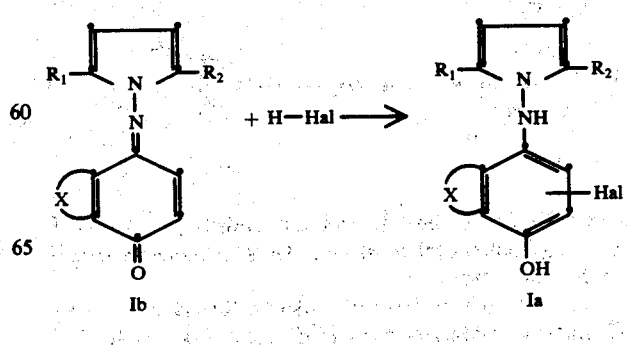

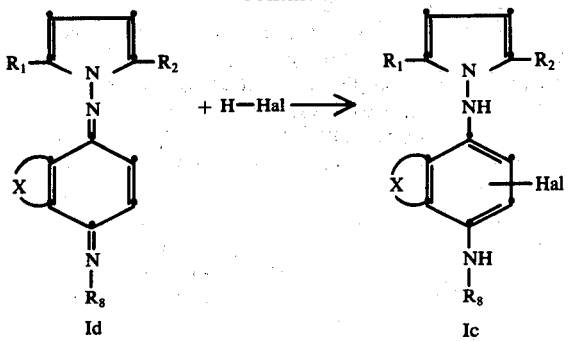

where $R_1$, $R_2$, $R_8$, X and Hal have the meanings given above.

The compounds of formulas Ib and Id where $R_3$ is halo (and n is 1) are prepared, as described above, by oxidation of the respective compounds of formulas Ia and Ic depicted above. The latter, in addition to being useful as antibacterial agents, are also useful as intermediates for preparing the compounds of formulas Ib and Id where $R_3$ is azido or di-lower-alkylamino. The latter are prepared by reaction of the corresponding halo compounds in a lower-alkanol solution with an alkali metal azide or a di-lower-alkylamine, as the case may be. Reaction of the compounds of formulas Ib or Id with a di-lower-alkylamine takes place at ambient temperature, whereas reaction with an alkali metal azide preferably is carried out at the reflux temperature of the lower-alkanol solvent.

The compounds of formulas Ib and Id where $R_3$ is amino are prepared by reducing the corresponding compounds where $R_3$ is azido with an alkali metal hydrosulfite followed by reaction of the resulting corresponding respective compound of formulas Ia or Ic with aqueous alkali at ambient temperature.

In a standard antibacterial screening procedure, the Autotiter method described by Goss et al., Applied Microbiology 16 (No. 9), 1414–1416 (1968), the compounds of formulas Ia, Ib, Ic and Id have been found to possess in vitro antibacterial activity thus indicating their usefulness as antibacterial agents. The compounds were thus found to be bactericidally effective against *Staphylococcus aureus*, three strains of *Escherichia coli*, *Klebsiella pneumoniae*, *Proteus mirabilis*, *Pseudomonas aeruginosa* and *Staphylococcus pyogenes* at concentrations from 1.6 to 500 mcg./ml. These results are surprising in view of the fact that the known analogous compound, 1-phenylamino-2,5-dimethylpyrrole having the formula:

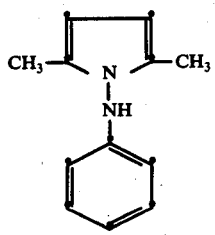

and disclosed by Reed, U.S. Pat. No. 2,725,378 was found to be inactive in the same test against the same organisms.

Some of the compounds of formulas Ia, Ib, Ic and Id have also been found active in an antitubercular activity screening test, thus indicating further usefulness of these particular species as antitubercular agents. The antitubercular screening procedure used is described briefly as follows: Female, Swiss mice weighing from 14 to 16 grams were used in all experiments. Groups of ten mice were used for each treated group with 20 mice in an infected control group. Infection of all mice was established by intravenous inoculation of 0.1 cc. of a 2 mg./cc. suspension of *Mycobacterium tuberculosis*, strain H37RV grown in Yoman's media for 2 weeks at 37.5° C. Test compounds were prepared as solutions at a pH near neutrality, and insoluble compounds were suspended in sterile 1% gum tragacanth. Medication was administered in a volume of 0.5 ml. either orally or subcutaneously twice daily and was initiated 48 hours post infection and continued for twenty days, twice daily. The control mice received sterile gum tragacanth. The mice were observed daily for 31 days, and deaths were recorded in terms of number of days of survival after infection. The average survival time of mice in each treatment group was calculated assigning a value of 31 days survival to all mice remaining alive at the time of termination of the experiment. The percent survival of mice in each treatment group was recorded, and the test was terminated 31 days after infection. All surviving mice were autopsied and lungs checked for lesions.

Some of the compounds of formulas Ia and Ib were also found active in a urinary antisepsis test, thus indicating further usefulness of these particular species as urinary antiseptic agents. The urinary antisepsis test is described briefly as follows: Female, Sprague-Dawley rats weighing from 160 to 200 grams were divided into groups of three and placed in plastic metabolism cages. Each group received 50 mg./kg. of the test compound at 8:00 a.m. and 50 mg./kg. at 4:00 p.m. The compound was suspended in gum tragacanth at a concentration which would allow the oral administration of 1 ml. of suspension for each 100 g. weight of the rat. The urine from each group of rats was collected for 24 hours starting at the time of the first medication. At the end of the collection period, the samples were measured, centrifuged for clarification, sterilized by ultrafiltration and frozen in sealed vials at −20° C. until they were thawed for testing against each of the bacterial and fungal organisms: *Staphylococcus aureus* Smith, *Escherichia coli* Vogel, *Proteus mirabilis* MGH-1, *Klebsiella pneumoniae* 39645, *Pseudomonas aeruginosa* MGH-2, *Trichophyton mentagrophytes*, *Aspergilla niger* and *Candida albicans*. Antibacterial activity of the urine samples was determined on the Autotiter by serial, two-fold dilutions of the urine in tryptose phosphate broth to which the bacterial inoculum was added. Dilutions of from 1:2 through 1:16,384 were tested. The inoculum was prepared by diluting an eighteen hour broth culture to a 0.1 optical density before diluting to 1:250 in tryptose phosphate broth. To indicate bacterial growth, 50 mcg./ml. of triphenyltetrazolium chloride was added to the inoculum, and after incubation at 37° C. for 18 hours, those dilutions in which bacterial growth had taken place showed a color change from colorless to red. The highest dilution without color change was recovered as the inhibitory dilution, and activity at the 1:2 dilution was not considered significant. Activity was considered to reside in dilutions at 1:4 or greater.

The actual determination of the numerical biological data definitive for particular compounds of formulas Ia, Ib, Ic and Id is readily made by standard test procedures by technicians versed in biological test procedures, without the need for any extensive experimentation.

The compounds of formulas Ia, Ib, Ic and Id can be formulated for use by preparing a dilute solution in an organic medium in which the compounds are soluble, for example ethyl alcohol or in such solution containing a surfactant, and are applied to a surface to be disinfected by conventional methods such as spraying, swabbing, immersion, and the like. Alternatively, the compounds can be formulated as ointments or cream bases, for example alkylpolyether alcohols, cetyl alcohol, stearyl alcohol, and the like, or as jellies by incorporating them in conventional jelly bases such as glycerol and tragacanth. They can also be formulated for use as aerosol sprays or foams or in conventional carriers, including sugars such as sucrose, lactose or maltose, for oral administration as tablets or capsules.

The molecular structures of the compounds of the invention were assigned on the basis of study of their infrared, ultraviolet, and NMR spectra, and confirmed by the correspondence between calculated and found values for elementary analyses for the elements.

The following examples will further illustrate the invention without, however, limiting it thereto. All melting points are uncorrected.

EXAMPLE 1

A solution of 61 g. (0.29 mole) of 4-benzyloxyphenylhydrazine [Bernini, Ann. chim. (Rome) 43, 559-60 (1953)] in 200 ml. of hot chloroform was added slowly to a solution of 20 ml. (0.36 mole) of acetaldehyde and 50 ml. of chloroform while maintaining the temperature below 22° C. The mixture was stirred for 1 hour, dried over anhydrous magnesium sulfate, and concentrated to dryness to give 78 g. of acetaldehyde 4-benzyloxyphenylhydrazone as an oil. The latter was dissolved in 100 ml. of pyridine, and the solution maintained at about 25° C. while 40 g. (0.29 mole) of benzoyl chloride was added with stirring over a period of fifteen minutes. The mixture was stirred at ambient temperature for about 1 hour, 500 ml. of water added, the mixture then filtered, and the solid filter washed with water and recrystallized from methanol to give two crops totaling 46 g. of acetaldehyde N-benzoyl-4-benzyloxyphenylhydrazone, m.p. 154°-156° C. and 158°-160° C.

A solution of 7.0 g. (0.02 mole) of the latter hydrazone and 2.8 g. (0.02 mole) of 2,5-dimethoxytetrahydrofuran in 25 ml. of glacial acetic acid was heated on a steam bath for 2 hours, then diluted with about 25 ml. of water and extracted with about 200 ml. of ethyl acetate. The extracts were washed first with saturated brine, then with saturated aqueous sodium bicarbonate, then dried and concentrated to dryness to give 7.6 g. of a dark solid which was recrystallized with charcoaling from cyclohexane to give 5.3 g. of 1-[N-benzoyl-N-(4-benzyloxyphenyl)amino]pyrrole, m.p. 120°-122° C.

The latter (47 g., 0.13 mole) was hydrolyzed by refluxing for about an hour and a half in a solution of 10.6 g. (0.16 mole) of potassium hydroxide in 100 ml. of methanol. The mixture was then concentrated to a small volume, diluted with about 200 ml. of water and extracted with diethyl ether. The extracts were dried, charcoaled and taken to dryness to give 32.5 g. of 1-(4-benzyloxyphenylamino)pyrrole as an oil. A small amount was crystallized from hexane to give material having m.p. 68°-70° C.

A solution of 30 g. (0.11 mole) of the latter in 170 ml. of ethanol was reduced over 3.0 g. of 10% palladium-on-charcoal in a Parr hydrogenator at room temperature under an initial hydrogen pressure of 47 p.s.i. When reduction was complete, the catalyst was removed by filtration and the solution concentrated to dryness to give 20 g. of an oil. The latter was dissolved in diethyl ether and the solution extracted with dilute sodium hydroxide. The combined alkaline extracts were acidified with dilute hydrochloric acid, the mixture extracted with diethyl ether, and the organic extracts washed with brine, and taken to dryness to give 17 g. of an oil which was distilled in vacuo to give 10.7 g. of 1-(4-hydroxyphenylamino)pyrrole, b.p. 143°-7° C./0.02 mm, which solidified to give material having m.p. 99°-102° C.

Proceeding in a manner similar to that described in Example 1, there was also obtained the following compound of formula Ia:

1A. 1-(4-Methoxyphenylamino)pyrrole (b.p. 117°-119° C./0.05 mm., m.p. 38°-40° C.) prepared by reaction of 38 g. of 4-methoxyphenylhydrazine with 19 ml. of acetaldehyde in 175 ml. of chloroform; reaction of the resulting acetaldehyde 4-methoxyphenylhydrazone with 40 g. of benzoyl chloride in the presence of 100 ml. of pyridine; reaction of the resulting acetaldehyde N-benzoyl-4-methoxyphenylhydrazone 35.5 g., m.p. 193°-196° C. from methanol) with hydrochloric acid; reaction of the resulting N-benzoyl-4-methoxyphenylhydrazine hydrochloride with 17 g. of 2,5-dimethoxytetrahydrofuran in 130 ml. of glacial acetic acid containing 10.6 g. of sodium acetate; and hydrolysis of 17.5 g. of the resulting (25 g.) 1-[N-benzoyl-N-(4-methoxyphenyl)amino]pyrrole (m.p. 88°-89° C. from cyclohexane).

EXAMPLE 2

A solution of 51.6 g. (0.30 mole) of N-methyl-4-hydroxyaniline hemisulfate in 45 ml. of concentrated hydrochloric acid was treated with 120 g. of ice, and the temperature of the mixture maintained at less than 10° C. while a solution of 21 g. (0.31 mole) of sodium nitrite in 75 ml. of water was added with stirring over a period of 15 minutes. When addition was complete, the mixture was stirred for an additional hour at around 10° C. and then extracted with ethyl acetate. The organic extracts were dried and taken to dryness to give 44.5 g. of N-methyl-N-nitroso-4-hydroxyaniline, m.p. 132°-134° C.

The latter (38.5 g., 0.25 mole) dissolved in 150 ml. of dimethylformamide (hereinafter DMF) was added with cooling and stirring over a period of fifteen minutes to a mixture of 12 g. (0.29 mole) of a 57% mineral oil dispersion of sodium hydride in 150 ml. of benzene. When addition was complete, a solution of 36.0 g. (0.29 mole) of benzyl chloride in 50 ml. of benzene was added and the mixture allowed to stand for several days. The mixture was treated with an approximately equal volume of water, extracted with ethyl acetate, and the extracts were dried and evaporated to dryness to give 63 g. of a solid which was recrystallized from cyclohexane to give 52.8 g. of N-methyl-N-nitroso-4-benzyloxyaniline, m.p. 95°-97° C.

The latter (55 g., 0.23 mole) dissolved in 400 ml. of tetrahydrofuran was added over a period of about thirty minutes to a stirred mixture of 8.5 g. (0.23 mole) of lithium aluminum hydride in 300 ml. of tetrahydrofuran while maintaining the temperature around 30°-40° C. When addition was complete, the mixture was stirred for one hour, then treated with 10 ml. of isopropanol, then 200 ml. of 30% sodium hydroxide, and the mixture filtered. The organic layer was separated from the filtrate and concentrated to dryness to give 51.5 g. of an oil which slowly solidified and was recrystallized from cyclohexane to give 38.7 g. of N-methyl-N-(4-benzyloxyphenyl)hydrazine.

The latter (2.3 g., 0.01 mole) was added in small portions over a period of about 5 minutes to a hot solution of 1.5 g. (0.011 mole) of 2,5-dimethoxytetrahydrofuran in 5.0 ml. of glacial acetic acid. The mixture was heated an additional 10 minutes on a steam bath, then poured into 100 ml. of ice water, and the mixture extracted with diethyl ether. The ether extracts, on drying and concentration to dryness, afforded 1.8 g. of an oil which was combined with 2.0 g. of material obtained in another, similar run and distilled in vacuo to give 2.3 g. of 1-[N-methyl-N-(4-benzyloxyphenyl)amino]pyrrole, b.p. 165°–176° C./0.03 mm.

The latter (15.4 g., 0.055 mole) was dissolved in 85 ml. of ethanol and reduced with hydrogen over 10% palladium-on-charcoal using the procedure described above in Example 1. There was thus obtained 7.5 g. of 1-[N-methyl-N-(4-hydroxyphenyl)amino]pyrrole, m.p. 70°–72° C. (recrystallized from cyclohexane).

EXAMPLE 3

To a stirred suspension of 5.0 g. (0.12 mole) of a 57% mineral oil dispersion of sodium hydride in 100 ml. of DMF was added portionwise, over a period of about ten minutes, 29.3 g. (0.096 mole) of N-benzoyl-4-benzyloxyaniline [Blatter, U.S. Pat. No. 3,165,529], and the mixture stirred for 1 hour. The mixture was then treated all at once with a solution of chloramine which was prepared from 260 ml. of Clorox (5.25% aqueous sodium hypochlorite) and 42 ml. of concentrated ammonium hydroxide in one liter of diethyl ether using the procedure described by Theilacker et al., Angew. Chem. 72, 127 (1960). The resulting mixture was stirred for four hours, then filtered and the filtrate washed with saturated brine. The crystalline material which separated at this point was collected and converted to the hydrochloride salt in ethanol with ethanolic hydrogen chloride to give 20 g. of N-benzoyl-N-(4-benzyloxyphenyl)hydrazine hydrochloride, m.p. 191°–193° C.

A solution of the latter (24 g., 0.068 mole), 8.5 g. (0.072 mole) of 2,5-hexanedione and 5.8 g. (0.071 mole) of sodium acetate in 75 ml. of glacial acetic acid was heated with stirring on a steam bath for 1 hour, then concentrated and extracted with ethyl acetate. The organic extracts were washed with saturated aqueous sodium bicarbonate, dried and concentrated to dryness to give 24 g. of an oil which was crystallized from hexane to give 20 g. of 1-[N-benzoyl-N-(4-benzyloxyphenyl)amino]2,5-dimethylpyrrole, m.p. 110°–112° C. Using the procedure described above in Example 1, the latter (20 g., 0.05 mole) was hydrolyzed with methanolic potassium hydroxide to give 15.8 g. of 1-(4-benzyloxyphenylamino)-2,5-dimethylpyrrole, m.p. 98°–100° C. (from cyclohexane) which was catalytically debenzylated to give 4.3 g. of 1-(4-hydroxyphenylamino)-2,5-dimethylpyrrole, m.p. 127°–129° C. (from cyclohexane and sublimation at 150° C./0.05 mm.).

Proceeding in a manner similar to that described in Example 3, there was also obtained the following compounds of formula Ia:

3A. 1-(3-Hydroxyphenylamino)pyrrole (m.p. 133°–135° C.) (sublimed) prepared by reaction of 50 g. of 3-benzyloxyaniline with 33 ml. of benzoyl chloride in 250 ml. of pyridine; reaction of the resulting N-benzoyl-3-benzyloxyaniline (74 g., m.p. 108°–110° C.) with 12 g. of a 57% sodium hydride in mineral oil dispersion and 0.65 mole of chloramine in DMF; reaction of the resulting N-benzoyl-N-(3-benzyloxyphenyl)hydrazine hydrochloride (40 g., m.p. 138°–141° C.) with 22.5 g. of 2,5-diethoxytetrahydrofuran and 9.0 g. of sodium acetate in 100 ml. of glacial acetic acid; hydrolysis with methanolic potassium hydroxide of the resulting 1-[N-benzoyl-N-(3-benzyloxyphenyl)amino]pyrrole (38.7 g.); and catalytic debenzylation of the resulting 1-(3-benzyloxyphenylamino)pyrrole (27.7 g., oil) with hydrogen over palladium-on-charcoal.

3B. 1-(2-Hydroxyphenylamino)pyrrole (m.p. 98°–100° C.) prepared by reaction of 32.5 g. of N-benzoyl-2-hydroxyaniline [Raiford, J. Am. Chem. Soc. 41, 2068–80 (1919)] with 0.16 mole of sodium hydride and 19 g. of benzyl chloride in DMF; reaction of the resulting N-benzoyl-2-benzyloxyaniline (44.5 g., oil) with 0.16 mole of sodium hydride and 0.39 mole of chloramine in DMF; reaction of the resulting N-benzoyl-N-(2-benzyloxyphenyl)hydrazine hydrochloride (47 g., m.p. 94°–97° C.) with 24 g. of 2,5-diethoxytetrahydrofuran in glacial acetic acid in the presence of 11 g. of sodium acetate; hydrolysis of the resulting 1-[N-benzoyl-N-(2-benzyloxyphenyl)amino]pyrrole 49 g. oil) with methanolic potassium hydroxide; and catalytic debenzylation of the resulting 1-(2-benzyloxyphenylamino)pyrrole (27.5 g., oil) with hydrogen over palladium-on-charcoal.

3C. 1-(3,4-Dihydroxyphenylamino)pyrrole (m.p. 122°–124° C. from benzene) prepared by reaction of 44 g. of 3,4-dibenzyloxyaniline [Balaban, J. Chem. Soc. 132, 1088–1093 (1929)] with 22 g. of benzoyl chloride in pyridine; reaction of the resulting N-benzoyl-3,4-dibenzyloxyaniline (34 g., m.p. 152°–153° C.) with 0.1 mole of sodium hydride and 0.26 mole of chloramine; reaction of the resulting N-benzoyl-N-(3,4-dibenzyloxyphenyl)hydrazine hydrochloride (28 g., m.p. 154°–159° C. from ethanol) with 11 g. of 2,5-diethoxytetrahydrofuran in glacial acetic acid in the presence of 5 g. of sodium acetate; hydrolysis with methanolic potassium hydroxide of the resulting 1-[N-benzoyl-N-(3,4-dibenzyloxyphenyl)amino]pyrrole (28.5 g., oil) and catalytic debenzylation of the resulting 1-(3,4-dibenzyloxyphenylamino)pyrrole (19.5 g., oil) with hydrogen over palladium-on-charcoal.

3D. 1(4-Hydroxy-1-naphthylamino)pyrrole (m.p. 148°–150° C., from diethyl ether/pentane) prepared by reaction of 90.5 g. of N-benzoyl-4-hydroxy-1-naphthylamine [Mishida et al., Sen-i Gakkaishi 25 (3), 141–143 (1969); C.A. 72, 13798c (1970)] with 0.35 mole of sodium hydride and 60 g. of benzyl bromide in DMF; reaction of the resulting N-benzoyl-4-benzyloxy-1-naphthylamine (105 g., m.p. 170°–173° C.) with 0.33 mole of sodium hydride and 0.8 mole of chloramine; reaction of the resulting N-benzoyl-N-(4-benzyloxy-1-naphthyl)hydrazine (75 g., m.p. 182°–183° C. from ethanol/ethyl acetate) with 29 g. of 2,5-dimethoxytetrahydrofuran in glacial acetic acid; hydrolysis with methanolic potassium hydroxide of the resulting 1-[N-benzoyl-N-(4-benzyloxy-1-naphthyl)amino]pyrrole (94 g., oil); and catalytic debenzylation of the resulting 1-(4benzyloxy-1-naphthylamino)pyrrole (m.p. 137°–139° C. from benzene/pentane) with hydrogen over palladium-on-charcoal.

3E. 1-(4-Phenylaminophenylamino)pyrrole (m.p. 110°-112° C., from cyclohexane) prepared by reaction of 25 g. of N-phenyl-p-phenylenediamine hydrochloride with 16.8 g. of benzoyl chloride in 100 ml. of pyridine; reaction of the resulting N-phenyl-N'-benzoyl-p-phenylenediamine (29.7 g., m.p. 160°-162° C.) with 0.12 mole of sodium hydride and 0.26 mole of chloramine; reaction of the resulting N-benzoyl-N-(4-phenylaminophenyl)hydrazine (28.5 g., oil) with 14 g. of 2,5-dimethoxytetrahydrofuran in 50 ml. of glacial acetic acid; and hydrolysis with methanolic potassium hydroxide of the resulting 1[N-benzoyl-N-(4-phenylaminophenyl)amino]pyrrole (18 g., oil).

3F. 1-(4-Methylaminophenylamino)pyrrole (m.p. 174°-176° C., from aqueous ethanol) prepared by reaction of 60.8 g. of N-methyl-4-nitroaniline with 88 g. of trifluoroacetic anhydride in 200 ml. of pyridine; catalytic reduction over 1.5 g. of 10% palladium-on-charcoal of the resulting N-methyl-N-trifluoroacetyl-4-nitroaniline 98 g., m.p. 129°-131° C.); reaction of the resulting N-methyl-N-trifluoroacetyl-p-phenylenediamine (87 g.) with 58 g. of benzoyl chloride in 215 ml. of pyridine; hydrolysis with ethanolic potassium hydroxide of the resulting N-methyl-N-trifluoroacetyl-N'-benzoyl-p-phenylenediamine (126 g., m.p. 128°-130° C.); reaction of 42.5 g. of the resulting N-methyl-N'-benzoyl-p-phenylenediamine (85 g., m.p. 202°-204° C.) with 0.22 mole of sodium hydride and 0.52 mole of chloramine; reaction of the resulting N-benzoyl-N-(4-methylaminophenyl)hydrazine (40 g., oil) with 30 g. of 2,5-dimethoxytetrahydrofuran in 150 ml. of glacial acetic acid; and hydrolysis with methanolic potassium hydroxide of the resulting 1-[N-benzoyl-N-(4-methylaminophenyl)amino]pyrrole (18 g.).

3G. 1-[4-(4-Chlorophenylamino)phenylamino]pyrrole (m.p. 123°-125° C., from cyclohexane) prepared by reaction of 53 g. of 4-nitrosophenol with 49 g. of 4-chloroaniline in the presence of 11 g. of p-toluenesulfonic acid in 300 ml. of methanol followed by treatment with 23 g. of sodium bicarbonate in 300 ml. of water; catalytic reduction over 1.0 g. of palladium-on-charcoal of the resulting (65 g.) 4-chloro-4'-nitrosodiphenylamine (m.p. 151°-154° C.); reaction of the resulting N-(4-chlorophenyl)-p-phenylenediamine (60 g., oil) with 40 g. of benzoyl chloride in 300 ml. of pyridine; reaction of the resulting N-benzoyl-N'-(4-chlorophenyl)-p-phenylenediamine (77 g., m.p. 180°-183° C.) with 0.29 mole of sodium hydride and 0.62 mole of chloramine; reaction of the resulting N-benzoyl-N-[4-(4-chlorophenylamino)phenyl]hydrazine (51 g.) with 23 g. of 2,5-dimethoxytetrahydrofuran in glacial acetic acid; and hydrolysis with methanolic potassium hydroxide of the resulting 1-{N-benzoyl-N-[4-(4-chlorophenylamino)phenyl]amino}pyrrole (50 g., oil).

3H. 1-[4-(4-Methoxyphenylamino)phenylamino]pyrrole, (m.p. 101°-103° C., from cyclohexane) prepared by reaction of 53 g. of 4-nitrosophenol with 48 g. of 4-methoxyaniline in the presence of 11 g. of p-toluenesulfonic acid in 300 ml. of methanol followed by treatment with 23 g. of sodium bicarbonate in 300 ml. of water; catalytic reduction over 2 g. of 10% palladium-on-charcoal of the resulting 4-methoxy-4'-nitrosodiphenylamine (62 g., m.p. 165°-167° C.); reaction of the resulting N-(4-methoxyphenyl)-p-phenylenediamine (58 g.) with 28 g. of benzoyl chloride in 300 ml. of pyridine; reaction of the resulting N-benzoyl-N'-(4-methoxyphenyl)-p-phenylenediamine (48 g.) with 0.18 mole of sodium hydride and 0.39 mole of chloramine; reaction of the resulting N-benzoyl-N-[4-(4-methoxyphenylamino)phenyl]hydrazine (47 g., oil) with 20 g. of 2,5-dimethoxytetrahydrofuran in glacial acetic acid; and hydrolysis with methanolic potassium hydroxide of the resulting 1-{N-benzoyl-N-[4-(4-methoxyphenylamino)phenylamino]}pyrrole (27 g., oil).

3J. 1-[4-(3,4-Dichlorophenylamino)phenylamino]pyrrole, (m.p. 112°-114° C., b 5.5 g. from cyclohexane) prepared by reaction of 79 g. of 3,4-dichloroaniline with 67 g. of 4-nitrosophenol in the presence of 14 g. of p-toluenesulfonic acid in 380 ml. of methanol followed by treatment with 29 g. of sodium bicarbonate in 380 ml. of water; catalytic reduction over 3 g. of 5% palladium-on-charcoal of the resulting 3,4-dichloro-4'-nitrosodiphenylamine (100 g., m.p. 173°-175° C.); reaction of the resulting N-(3,4-dichlorophenyl)-p-phenylenediamine (76 g.) with 36 ml. of benzoyl chloride in 300 ml. of pyridine; reaction of the resulting N-benzoyl-N'-(3,4-dichlorophenyl)-p-phenylenediamine (98 g.) with 0.34 mole of sodium hydride and 0.66 mole of chloramine; reaction of the resulting N-benzoyl-N-[4-(3,4-dichlorophenylamino)phenyl]hydrazine (120 g., oil) with 46 g. of 2,5-dimethoxytetrahydrofuran in glacial acetic acid; and hydrolysis with methanolic potassium hydroxide of the resulting 1-{N-benzoyl-N-[4-(3,4-dichlorophenylamino)phenylamino]}pyrrole (108 g., oil).

3K. 1-(Phenylamino)pyrrole, (m.p. 44°-46° C., from pentane) prepared by reaction of 24.8 g. of N-benzoyl-N-phenylhydrazine hydrochloride with 13.2 g. of 2,5-dimethoxytetrahydrofuran in glacial acetic acid and hydrolysis with methanolic potassium hydroxide of the resulting 1-(N-benzoyl-N-phenylamino)pyrrole (19.5 g., m.p. 109°-110° C.).

EXAMPLE 4

A solution of 18 g. (0.068 mole) of 1-(4-benzyloxyphenylamino)pyrrole (described above in Example 1) in 100 ml. of diethyl ether was treated slowly over a period of about 30 minutes with a solution of 10 g. (0.078 mole) of oxalyl chloride in 150 ml. of diethyl ether while maintaining the temperature around −20° C. The mixture was then stirred at room temperature for about one hour, and the solid which separated was collected and dried to give 13.3 g. of 2-(4-benzyloxyphenyl)pyrrolo[1,2-b]pyrazole-3,4-dione.

The latter was dissolved by warming in a solution of 110 ml. of 2N sodium hydroxide and 150 ml. of water and the solution treated dropwise with 15 ml. of 30% hydrogen peroxide. The mixture was stirred at room temperature overnight and then acidified with concentrated hydrochloric acid and extracted with ethyl acetate. The organic extracts, on drying and concentration in vacuo, afforded solid material which was recrystallized from benzene/pentane to give 10 g. of 1-(4-benzyloxyphenylamino)pyrrole-2-carboxylic acid, m.p. 158°-159° C. The latter (9.2 g., 0.03 mole), on catalytic debenzylation over palladium-on-charcoal as described above, afforded 3.1 g. of 1-(4-hydroxyphenylamino)pyrrole-2-carboxylic acid, m.p. 154° C. (dec., from diethyl ether/pentane).

EXAMPLE 5

A solution of 24 g. (0.29 mole) of 1-aminopyrrole [Epton, Chem. Ind. (London) 10, 425–426 (1965)] in 500 ml. of water and 50 ml. of 2N hydrochloric acid was treated with a solution of 33 g. (0.3 mole) of p-benzoquinone in two liters of water and the mixture allowed to stand at room temperature for about fifteen minutes.

The solid which separated was then collected, washed with water, dried and recrystallized from cyclohexane to give 15.5 g. of 1-(1,4-benzoquinon-1-ylimino)pyrrole, m.p. 89°-91° C.

By proceeding in a manner similar to that described in Example 5, there was obtained the following compounds of formula Ib:

5A. 1-(3,5-Di-tert.-butyl-1,4-benzoquinon-1-ylimino)-pyrrole, (m.p. 77° C.) prepared from 5.0 g. of 1-aminopyrrole and 8.8 g. of 2,6-di-tert.-butyl-1,4-benzoquinone.

5B. 1-(3,5-Dimethyl-1,4-benzoquinon-1-ylimino)pyrrole, (m.p. 68° C. from pentane) prepared from 8.0 g. of 1-aminopyrrole and 9.0 g. of 2,6-dimethyl-1,4-benzoquinone.

EXAMPLE 6

A mixture of 10.7 g. (0.05 mole) of 1-(4-hydroxyphenylamino)-2,5-dimethylpyrrole (described above in Example 3) and 22 g. (0.102 mole) of mercuric oxide in 200 ml. of benzene was heated under reflux for about 30 minutes, then filtered and the filtrate taken to dryness to give 10.3 g. of an oil which was distilled in vacuo to give 1.6 g. of 1-(1,4-benzoquinon-1-ylimino)-2,5-dimethylpyrrole, b.p. 94°-122° C./0.1 mm., which slowly solidified to give material having m.p. 50°-54° C.

In a similar manner, using the procedure described in Example 6, there can be obtained the following compounds of formula Ib:

6A. 1-(1,4-Naphthoquinon-1-ylimino)pyrrole, (m.p. 83°-84° C., from diethyl ether) by oxidation with 15 g. of mercuric oxide in 150 ml. benzene of 8.0 g. of the 1-(4-hydroxy-1-naphthylamino)pyrrole described above in Example 3D (yield 4.7 g.).

6B. 1-(1,4-Benzoquinon-1-ylimino)pyrrole-2-carboxylic acid by oxidation with mercuric oxide in benzene of the 1-(4-hydroxyphenylamino)pyrrole-2-carboxylic acid described above in Example 4.

EXAMPLE 7

To a solution of 8.7 g. (0.05 mole) of 1-(4-hydroxyphenylamino)pyrrole (described in Example 1) in 50 ml. of pyridine was slowly added 15.0 g. (0.107 mole) of benzoyl chloride while cooling the reaction in an ice bath. The mixture was then diluted with water, extracted with diethyl ether and the ether extracts washed with dilute hydrochloric acid and then with saturated aqueous sodium bicarbonate. The solid which separated from the solution was collected and recrystallized from carbon tetrachloride to give 2.7 g. of 1-[N-benzoyl-N-(4-benzoyloxyphenyl)amino]pyrrole, m.p. 167°-168° C.

7A. Following a procedure similar to that described in Example 7, 8.7 g. (0.05 mole) of 1-(4-hydroxyphenylamino)pyrrole was reacted with 17.0 g. (0.11 mole) of 4-methylbenzoyl chloride in 50 ml. of pyridine to give 3.7 g. of 1-{N-[4-methylbenzoyl]N-[4-(4-methylbenzoyloxy)phenyl]amino}pyrrole, m.p. 178°-180° C. (from ethyl acetate).

EXAMPLE 8

To a solution of 5 g. (0.029 mole) of 1-(4-hydroxyphenylamino)pyrrole in 29 ml. of pyridine was added dropwise with stirring 4.5 g. (0.029 mole) of 4-methylbenzoyl chloride. The product was precipitated from the reaction mixture by dilution with water and the crude product recrystallized from cyclohexane to give 7.3 g. of 1-{N-[4-(4-methylbenzoyloxy)phenyl]amino}•pyrrole, m.p. 137°-139° C.

EXAMPLE 9

To a solution of 10 g. (0.058 mole) of 1-(4-hydroxyphenylamino)pyrrole in 50 ml. of pyridine at ambient temperature was added 15 g. of acetic anhydride. The mixture was worked up in the manner described above in Example 7 and the product purified by distillation in vacuo to give 5.1 g. of 1-(4-acetoxyphenylamino)pyrrole, b.p. 128°-134° C./0.1 mm.; m.p. 88°-91° C.

EXAMPLE 10

To a slurry of 1.5 g. of a 57% mineral oil dispersion of sodium hydride in 25 ml. of DMF at about 10° C. was added a solution of 6.0 g. of 1-(4-acetoxyphenylamino)pyrrole (described in Example 9) in 25 ml. of DMF. When addition was complete, the mixture was treated in portions with 3.5 g. of acetic anhydride, stirred in an ice bath for 1 hour and then worked up in the manner described in Example 7. The product was recrystallized from cyclohexane to give 3.8 g. of 1-[N-acetyl-N-(4-acetoxyphenyl)amino]pyrrole, m.p. 108°-111° C.

EXAMPLE 11

To a warm solution of 230 g. (2.15 moles) of benzoquinone in 2 liters of 95% ethanol containing 5 ml. of trifluoroacetic acid was added dropwise over a period of 30 minutes a solution of 84 g. (1.02 mole) of 1-aminopyrrole in 80 ml. of ethanol. The mixture was then diluted with 12 liters of water, and the solid which separated was collected, dissolved in about 7 liters of hot hexane, concentrated to a volume of about 2 liters, charcoaled, filtered and cooled. The solid which separated was collected and dried to give 93 g. of 1-(1,4-benzoquinon-1-ylimino)pyrrole, m.p. 94°-96° C., identical with that described above in Example 5.

The combined filtrates from the latter were taken to dryness, and the residue leached with ether. The ether insoluble material was recrystallized from DMF to give 2.0 g. of 1,1'-(1,4-benzoquinonyldiimino)dipyrrole, m.p. 169°-171° C., which from its NMR spectrum was determined to have the anti-configuration.

In a separate run in which 0.90 mole of 1-aminopyrrole was reacted with 0.43 mole of benzoquinone in 700 ml. of diethyl ether containing about 2 ml. of trifluoroacetic acid, a total of 42.6 g. of the same anti-1,1'-(1,4-benzoquinonyldiimino)dipyrrole, m.p. first crop 162°-164° C. (32 g.), m.p. second crop 165°-167° C. (10.6 g.), was obtained. A third crop consisting of 26.7 g. of solid material was obtained on further evaporation of the combined mother liquors from the first two crops. This material was dried, ground in a mortar and then stirred for one hour at room temperature with ethyl acetate. The mixture was then filtered, and the filtrate was concentrated, without heating, to a volume of about 50 ml. The solid which separated was collected and dried to give 7.5 g. of material having m.p. 110°-112° C. (resolidifies and melts again 162-163). This material was determined from its NMR spectrum and a comparison of the NMR spectrum obtained for the anti-form described above to be the syn form of 1,1'-(1,4-benzoquinonyldiimino)dipyrrole.

EXAMPLE 12

A solution of 2.2 g. of 1,1'-di-(1,4-benzoquinondi-1,4-ylimino)pyrrole in benzene was stirred well with an aqueous solution of 4 g. of sodium hydrosulfite. The organic layer was separated, charcoaled, taken to dryness and the residue recrystallized from isopropanol to give 1.0 g. of 1,1'-[(1,4-phenylene)diamino]dipyrrole, m.p. 178°–181° C.

EXAMPLE 13

A solution of 8.2 g. (0.1 mole) of 1-aminopyrrole, 6 g. (0.05 mole) of 2-methyl-p-benzoquinone and 10 drops of trifluoroacetic acid in 50 ml. of diethyl ether was allowed to stand at ambient temperature for 2 days, and the solid which separated (two crops) was collected and recrystallized from ethyl acetate to give 5 g. of 1,1'-(2-methyl-1,4-benzoquinonyldiimino)dipyrrole, m.p. 167°–169° C.

EXAMPLE 14

A solution of 15 g. (0.087 mole) of 1-(1,4-benzoquinon-1-ylimino)pyrrole (described in Example 5) in 600 ml. of diethyl ether was cooled in an ice bath while anhydrous hydrogen chloride was bubbled through the solution for 10 minutes. The solution was washed with water, then with saturated sodium bicarbonate, dried and concentrated to dryness to give 10 g. of crude product which was recrystallized from hexane to give 9 g. of 1-(2-chloro-4-hydroxyphenylamino)pyrrole, m.p. 77°–80° C.

EXAMPLE 15

To a solution of 17 g. (0.1 mole) of silver nitrate in 1400 ml. of ethanol was added a solution of 19 g. (0.09 mole) of 1-(2-chloro-4-hydroxyphenylamino)pyrrole in 100 ml. of ethanol. The mixture was stirred for three hours, concentrated to a volume of about 200 ml., diluted with 600 ml. of water and extracted with diethyl ether. The ether extracts were washed with water, dried and concentrated to about 40 ml., cooled, and the solid which separated was collected to give 5.9 g. of 1-(2-chloro-1,4-benzoquinon-1-ylimino)pyrrole, m.p. 110°–111° C.

EXAMPLE 16

To a stirred solution of 12.5 g. (0.05 mole) of 1-(4-phenylaminophenylamino)pyrrole (described in Example 3E) in 200 ml. of acetone was added 25 g. (0.19 mole) of silver oxide. The mixture was stirred for 30 minutes, heated to reflux and filtered while hot. The filtrate was concentrated to about 100 ml. The solid which separated from the cooled mixture was collected and dried to give 9.5 g. of 1-(4-phenylimino-1,4-benzoquinon-1ylimino)pyrrole, m.p. 146°–147° C.

16A. Following a procedure similar to that described in Example 16, 5 g. of 1-[4-(4-methoxyphenylamino)phenylamino]pyrrole (described in Example 3H) in 75 ml. of acetone was oxidized with 8 g. of silver oxide and the product recrystallized from acetone to give 2.3 g. of 1-[4-(4-methoxyphenylimino)-1,4-benzoquinon-1-ylimino]pyrrole, m.p. 141°–143° C.

EXAMPLE 17

A mixture of 14 g. (0.11 mole) of 4-nitrosophenol and 3 g. (0.016 mole) of p-toluenesulfonic acid in 80 ml. of methanol was stirred at ambient temperature for 1 hour and then treated with 8.2 g. (0.1 mole) of 1-aminopyrrole. The mixture was stirred for an additional 3½ hours, treated with a solution of 6 g. (0.07 mole) of sodium bicarbonate in 80 ml. of water, stirred for an additional half hour, and the precipitated solid collected and chromatographed on silica gel using 1:4 ethyl acetate/hexane as eluant. The product thus isolated was recrystallized from benzene to give 6.2 g. of 1-(4-nitrosophenylamino)pyrrole, m.p. 77°–80° C.

EXAMPLE 18

To a warm solution of 5 g. (0.024 mole) of 1-(2-chloro-1,4-benzoquinon-1-ylimino)pyrrole (described in Example 15)in 100 ml. of ethanol was added a solution of 2 g. (0.04 mole) of dimethylamine in 25 ml. of ethanol. The mixture was allowed to stand at ambient temperature for 20 minutes, diluted with brine and extracted with ethyl acetate. The combined extracts were washed with brine, dried and concentrated to dryness to give 4.5 g. of an oil which was crystallized from carbon tetrachloride to give 2.4 g. of 1-(2-dimethylamino-1,4-benzoquinon-1-ylimino)pyrrole, m.p. 128°–130° C.

EXAMPLE 19

A solution of 5.1 g. (0.024 mole) of 1-(2-chloro-1,4-benzoquinon-1-ylimino)pyrrole (described in Example 15) in 100 ml. of ethanol was heated to about 60° C. and then treated with a solution of 3.2 g. (0.05 mole) of sodium azide. The mixture was heated at 55°–60° C. for about 20 minutes, then cooled, diluted with water and filtered to give solid material which was recrystallized from cyclohexane to give 2.7 g. of 1-(2-azido-1,4-benzoquinon-1ylimino)pyrrole, m.p. 104°–106° C.

EXAMPLE 20

A solution of 4.0 g. (0.019 mole) of 1-(2-azido-1,4-benzoquinon-1-ylimino)pyrrole (described in Example 19) and 4.0 g. of sodium hydrosulfite in 15 ml. of ethyl acetate and 20 ml. of water was stirred for one hour, the organic layer separated, dried and taken to dryness to give 4.0 g. of 1-(2-azido-4-hydroxyphenylamino)pyrrole.

The latter was dissolved in 50 ml. of ethyl acetate and 10 ml. of 2N sodium hydroxide, and the mixture was stirred under nitrogen for 1 hour. An additional 10 ml. of alkali was added, the mixture was stirred overnight, treated with an additional 10 ml. of alkali and stirred for an additional hour. The organic layer was then separated, dried over magnesium sulfate and taken to dryness to give a solid which was recrystallized from carbon tetrachloride to give 1.9 g. of 1-(2-amino-1,4-benzoquinon-1-ylmino)pyrrole, m.p. 163°–165° C.

BIOLOGICAL TEST RESULTS

Data obtained in in vitro antibacterial screening tests against the bacterial organisms Staphylococcus aureus(a), Escherichia coli [E. coli Vogel(b), E. coli AB 1932-1(c) and E. coli 1100/B22(d)], Klebsiella pneumoniae(e), Proteus mirabilis(f), Pseudomonas aeruginosa(g) and Staphylococcus pyogenes(h) using the procedure described by Goss et al., Applied Microbiology 16 (No. 9), 1414–1416 (1968) for the compounds of the invention are given in the table below, the minimum inhibitory bactericidal concentration (MIC) being expressed in terms of micrograms/milliliter. The letter "I" designates inactive and the small letters (a)–(h) identify each of the test organisms in the columns of the table. For comparative purposes, results obtained in a parallel series of tests using the known reference compound 1-phenylamino-2,5-dimethylpyrrole (designated Ref.) are also included. As shown by the data, this compound was found to be inactive against all the above-indicated test organisms against which it was tested.

| Ex. | a | b | c | d | e | f | g | h |
|---|---|---|---|---|---|---|---|---|
| Ref. | I | I | — | — | I | I | I | — |
| 1 | 3.1 | 125 | — | — | 125 | 31.3 | 62.5 | — |
| 1A | I | I | — | — | I | I | I | — |
| 2 | 125 | I | — | — | I | I | I | — |
| 3 | 3.1 | I | — | — | 125 | 15.6 | 62.5 | — |
| 3A | 62.5 | 500 | — | — | 500 | 500 | 500 | — |
| 3B | 3.1 | 125 | — | — | 125 | 15.6 | 62.5 | — |
| 3C | 1.6 | I | — | — | 125 | 62.5 | I | — |
| 3D | 12.5 | I | — | — | 125 | 62.5 | 125 | — |
| 3E | 31.3 | I | I | I | 250 | I | I | 31.3 |
| 3F | 62.5 | I | I | I | I | I | I | 250 |
| 3G | 3.9 | I | I | I | I | I | I | 15.6 |
| 3H | 125 | I | I | I | I | I | I | 125 |
| 3K | >250 | >125 | — | — | >125 | >125 | >125 | — |
| 4 | 31.3 | 250 | — | — | I | 125 | 125 | — |
| 5 | 6.3 | 125 | — | — | 125 | 62.5 | 62.5 | — |
| 5A | I | I | — | — | I | I | I | — |
| 5B | 31.3 | I | — | — | I | I | I | — |
| 6 | 12.5 | I | — | — | I | 62.5 | 62.5 | — |
| 6A | 7.8 | I | — | — | I | I | I | — |
| 7 | 125 | I | — | — | 62.5 | I | 62.5 | — |
| 7A | 125 | I | — | — | 62.5 | I | I | — |
| 8 | I | I | I | I | I | I | I | I |
| 9 | 250 | I | — | — | I | I | I | — |
| 10 | I | I | — | — | I | I | I | — |
| 11(anti) | I | 62.5 | — | — | 62.5 | 31.3 | 62.5 | — |
| 11(syn) | >62.5 | >62.5 | >62.5 | >62.5 | >62.5 | >125 | >62.5 | >62.5 |
| 12 | 125 | I | I | I | I | I | I | I |
| 13 | I | I | I | I | I | I | 62.5 | 62.5 |
| 14 | 62.5 | I | I | I | I | I | I | 125 |
| 15 | 81.3 | I | I | I | I | I | I | 62.5 |
| 16 | I | I | I | I | I | I | 62.5 | 62.5 |
| 16A | I | I | I | I | I | I | 125 | 125 |
| 17 | 125 | 250 | 500 | 125 | 500 | 250 | 500 | 62.5 |
| 18 | 62.5 | >125 | >125 | >125 | >125 | >125 | >125 | 62.5 |
| 19 | 125 | >125 | >125 | >250 | >125 | >250 | >125 | 125 |
| 20 | 15.6 | 125 | 125 | 125 | >125 | 125 | 125 | 15.6 |

The compounds of the invention which are active against the two gram positive test organisms, Staphyloindistinguishable. Doses are in mg./kg. (oral administration).

| | | | Survivors/Total | | | |
|---|---|---|---|---|---|---|
| Dose | Ex.1 | Ex.3G | Ex.5 | Ex.5A | Ex.11(anti) | Ex.11(syn) | Ex.16 |
| 0.39 | 0/10 | — | — | — | — | — | — |
| 0.78 | 1/10 | — | — | — | — | — | — |
| 1.5 | 0/10 | — | 0/10 | — | 10/10 | — | — |
| 3.1 | 0/10 | 0/10 | 0/10 | — | 7/10 | 7/10 | — |
| 6.25 | 3/10 | 4/10 | 6/10 | — | 9/10 | 10/10 | — |
| 12.5 | 10/10 | 5/10 | 10/10 | — | 8/10 | 8/10 | — |
| 25 | 10/10 | 9/10 | 10/10 | — | 10/10 | 10/10 | — |
| 50 | 10/10 | 7/10 | 10/10 | 9/10 | 7/10 | 10/10 | 3/10 |
| 100 | — | 10/10 | — | — | — | — | — |
| 200 | — | — | — | 5/10 | — | — | 6/10 | coccus aureus and Staphylococcus pyogenes (identified as organisms a and h in the above table), are generally useful as surface disinfectants against non-pathogenic organisms. On the other hand, the compounds which are active against the remainder of the test organisms (b through g in the table), which are all gram negative organisms, are generally useful against infections of a pathogenic origin such as urinary tract infections.

Certain of the species of formulas Ia, Ib, Ic and Id have anti-tuberculosis activity. Data so-obtained are given below. It will be noted that, whereas the anti form of 1,1'-(1,4-benzoquinonyldiimino)dipyrrole, described in Example 11, shows good activity against gram negative baceteria in the in vitro test described above, the syn form is inactive against all test organisms in the same test procedure. Yet in the in vivo anti-tuberculosis test, these two forms are both active and are virtually Certain of the species of formulas Ia and Ib have also been found to have urinary antiseptic activity. Data, expressed in terms of inhibitory dilutions, so-obtained are given below, the letter "I" designating Inactive. It will be noted that 1-(phenylamino)pyrrole, described in Example 3K, although as shown above it was found inactive in in vitro tests against each of the organisms used in the test procedure, it is quite active in the in vitro urinary antiseptic test. This species is thus useful as a urinary antiseptic agent, and although outside the ambit of any of formulas Ia, Ib, Ic or Id as defined herein, is considered to be within the purview of the invention. The letters a–h at the head of the columns identify the test organisms Staphylococcus aureus Smith (a), Escherichia coli Vogel (b), Klebsiella pneumoniae 39645 (c), Proteus mirabilis MGH-1 (d), Pseudomonas aeruginosa MGH-2 (e), Trichophyton mentagrophytes (f), Aspergilla niger (g) and Candida albicans (h).

| | | | | Test Organism | | | | |
|---|---|---|---|---|---|---|---|---|
| Example | a | b | c | d | e | f | g | h |
| 1 | 1:32 | 1:2 | 1:2 | 1:16 | 1:2 | 1:64 | 1:2 | 1:2 |
| 1A | 1:32 | 1:4 | I | 1:16 | 1:2 | 1:8 | 1:2 | 1:2 |

-continued

| Example | a | b | c | d | e | f | g | h |
|---|---|---|---|---|---|---|---|---|
| 3 | 1:4 | I | I | I | I | 1:8 | 1:2 | 1:2 |
| 3C | 1:8 | >1:2 | >1:2 | >1:2 | >1:2 | 1:4 | >1:2 | >1:2 |
| 3K | 1:24 to 1:128 | 1:2 to 1:4 | I | 1:4 to 1:192 | 1:2 | I | — | I |
| 4 | 1:16 | I | I | 1:8 | I | I | I | I |
| 5 | 1:16 to 1:32 | 1:2 | I | 1:4 | I | 1:16 to 1:32 | 1:2 | 1:2 |
| 5B | 1:4 | I | I | I | I | I | 1:2 | 1:2 |
| 6 | 1:2 | 1:2 | 1:2 | I | 1:2 | 1:4 | I | I |

I claim:

1. A compound having the formula:

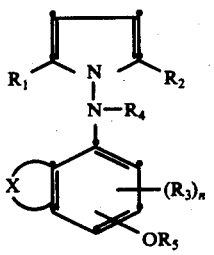

where $R_1$ and $R_2$ are each hydrogen or each lower-alkyl, or $R_1$ is hydrogen and $R_2$ is carboxyl; $R_3$ is hydrogen, hydroxy, benzyloxy, halo, azido, amino, di-lower-alkylamino or lower-alkyl; $R_4$ is hydrogen, lower-alkanoyl, benzoyl or lower-alkyl; X represents either a benzenoid nucleus fused to the phenyl ring at the positions indicated, or it represents two hydrogen atoms or one hydrogen atom and one of the groups $R_3$, or two of the groups $R_3$; $R_5$ is hydrogen, lower-alkyl, lower-alkanoyl, benzoyl or benzyl; and $n$ is one of the integers 1 and 2, and where the phenyl ring of the groups $R_4$ and $R_5$ when benzoyl can be substituted by lower-alkyl, lower-alkoxy or from one to two halogens, and where halo or halogen, all occurrences, represents fluorine, chlorine or bromine, and lower-alkyl, lower-alkoxy and lower-alkanoyl, all occurrences, have from one to four carbon atoms.

2. A compound according to claim 1 where $R_3$ is hydrogen, hydroxy or halogen; $R_4$ is hydrogen or lower-alkyl; X represents either a benzenoid nucleus fused to the phenyl ring at the positions indicated or it represents two hydrogen atoms; $R_5$ is hydrogen or lower-alkyl; and $n$ is the integer 1.

3. A compound according to claim 2 where $R_1$ and $R_2$ are each hydrogen or each lower-alkyl; $R_3$ is hydrogen or hydroxy; $R_4$ is hydrogen; and X represents two hydrogen atoms.

4. 1-(4-Methoxyphenylamino)pyrrole according to claim 3.

5. 1-(4-Hydroxyphenylamino)-2,5-dimethylpyrrole according to claim 3.

6. 1-(4-Hydroxyphenylamino)pyrrole according to claim 3.

7. 1-(3-Hydroxyphenylamino)pyrrole according to claim 3.

8. 1-(2-Hydroxyphenylamino)pyrrole according to claim 3.

9. 1-(3,4-Dihydroxyphenylamino)pyrrole according to claim 3.

10. 1-(4Hydroxy-1-naphthylamino)pyrrole according to claim 2.

11. 1-[N-Methyl-N-(4-hydroxyphenyl)amino]pyrrole according to claim 2.

12. 1(4-Hydroxyphenylamino)pyrrole-2-carboxylic acid according to claim 2.

* * * * *

UNITED STATES PATENT AND TRADEMARK OFFICE
CERTIFICATE OF CORRECTION

PATENT NO. : 4,051,147
DATED : September 27, 1977
INVENTOR(S) : Robert E. Johnson It is certified that error appears in the above-identified patent and that said Letters Patent are hereby corrected as shown below:

Column 5, line 60 reads "where $R_1$, $R_2$, $R_3$, $R_4$, $R_5$, $R_6$, $R_7$, $R_8$, X and n" and should read --where $R_1$, $R_2$, $R_3$, $R_4$, $R_5$, $R_7$, $R_8$, X and n--.

Column 10, line 3 reads "The final products of formulas 1b and 1b are prepared" should read --The final products of formulas 1b and 1d are prepared--.

Column 13, line 40 reads "Autotiter method" and should read --Autotiter®  method--.

Column 14, line 52 reads "Autotiter by serial," and should read --Autotiter® by serial,--.

Signed and Sealed this

Seventeenth Day of October 1978

[SEAL]

Attest:

RUTH C. MASON
Attesting Officer

DONALD W. BANNER
Commissioner of Patents and Trademarks